United States Patent
Khaiat et al.

(10) Patent No.: US 10,028,900 B2
(45) Date of Patent: Jul. 24, 2018

(54) PHOTOSTABLE SUNSCREEN COMPOSITION FOR TOPICAL APPLICATION

(71) Applicant: KANCOR INGREDIENTS LTD, Mumbai, Maharashtra (IN)

(72) Inventors: Alain Victor Khaiat, Singapore (SG); Shaju Asokan Vaikkathukattil, Kerala (IN); Ramesh Chandran Kalapurakkal, Kerala (IN); Prakash Kumar Unnikrishnan, Kerala (IN)

(73) Assignee: KANCOR INGREDIENTS LTD, Mumbai, Maharashtra (IN)

( * ) Notice: Subject to any disclaimer, the term of this patent is extended or adjusted under 35 U.S.C. 154(b) by 0 days.

(21) Appl. No.: 15/120,854

(22) PCT Filed: Mar. 27, 2015

(86) PCT No.: PCT/IN2015/000148
§ 371 (c)(1),
(2) Date: Aug. 23, 2016

(87) PCT Pub. No.: WO2015/145464
PCT Pub. Date: Oct. 1, 2015

(65) Prior Publication Data
US 2017/0065510 A1    Mar. 9, 2017

(30) Foreign Application Priority Data
Mar. 27, 2014    (IN) .......................... 1079/MUM/2014

(51) Int. Cl.
| | | |
|---|---|---|
| *A61K 8/49* | (2006.01) | |
| *A61K 8/27* | (2006.01) | |
| *A61K 8/29* | (2006.01) | |
| *A61K 8/35* | (2006.01) | |
| *A61K 8/37* | (2006.01) | |
| *A61K 8/44* | (2006.01) | |
| *A61Q 17/04* | (2006.01) | |
| *A61K 8/31* | (2006.01) | |
| *A61K 8/34* | (2006.01) | |
| *A61K 8/36* | (2006.01) | |
| *A61K 8/41* | (2006.01) | |
| *A61K 8/42* | (2006.01) | |
| *A61K 8/60* | (2006.01) | |
| *A61K 8/64* | (2006.01) | |
| *A61K 8/81* | (2006.01) | |
| *A61K 8/86* | (2006.01) | |
| *A61K 8/891* | (2006.01) | |
| *A61K 8/97* | (2017.01) | |

(52) U.S. Cl.
CPC .............. *A61K 8/4973* (2013.01); *A61K 8/27* (2013.01); *A61K 8/29* (2013.01); *A61K 8/31* (2013.01); *A61K 8/34* (2013.01); *A61K 8/342* (2013.01); *A61K 8/345* (2013.01); *A61K 8/347* (2013.01); *A61K 8/35* (2013.01); *A61K 8/361* (2013.01); *A61K 8/37* (2013.01); *A61K 8/41* (2013.01); *A61K 8/42* (2013.01); *A61K 8/445* (2013.01); *A61K 8/496* (2013.01); *A61K 8/4966* (2013.01); *A61K 8/60* (2013.01); *A61K 8/602* (2013.01); *A61K 8/64* (2013.01); *A61K 8/8194* (2013.01); *A61K 8/86* (2013.01); *A61K 8/891* (2013.01); *A61K 8/97* (2013.01); *A61Q 17/04* (2013.01); *A61K 2800/52* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,152,983 | A | * | 10/1992 | Nambudiry .............. A61K 8/35 424/59 |
| 5,244,665 | A | | 9/1993 | Natraj et al. |
| 5,292,529 | A | | 3/1994 | Gregory et al. |
| 2010/0143276 | A1 | | 6/2010 | Richard et al. |
| 2011/0200543 | A1 | | 8/2011 | Josso |

FOREIGN PATENT DOCUMENTS

| | | | |
|---|---|---|---|
| WO | 2012119860 A1 | 9/2012 | |
| WO | WO-2012119860 A1 * | 9/2012 | .............. A61K 8/35 |

OTHER PUBLICATIONS

United States Patent and Trademark Office (ISR/US), "International Search Report for PCT/IN2015/000148", US, dated Feb. 26, 2016.
DMS Nutritional Products Ltd. 2-Ethylhexyl Methoxycinnamate [CAS No. 5466-77-3] Comments to NTP Proposal release May 30, 2008.
DSM nutritional Products. PARSOL® 1789. Product Information. Released May 2005.

* cited by examiner

*Primary Examiner* — Robert A Wax
*Assistant Examiner* — Melissa Mercier
(74) *Attorney, Agent, or Firm* — Tim Tingkang Xia, Esq.; Locke Lord LLP

(57) ABSTRACT

The sunscreen composition includes dibenzoylmethane derivative in 1 to 5% by weight of the composition, octyl-methoxycinnamate in 1 to 10% by weight of the composition and dermatologically acceptable excipients in 79 to 97% by weight of the composition containing 60-75% aqueous phase stabilised with 1-(4-methoxy-5-benzofura-nyl)-3-phenyl 1, 3 propanedione (pongamol) in 0.9 to 6% by weight of the composition.

17 Claims, No Drawings

PHOTOSTABLE SUNSCREEN COMPOSITION FOR TOPICAL APPLICATION

CROSS-REFERENCE TO RELATED PATENT APPLICATIONS

This application is a U.S. national stage application of PCT patent application Ser. No. PCT/IN2015/000148, filed Mar. 27, 2015, which itself claims priority to and the benefit of Indian patent application Ser. No. 1079/MUM/2014, filed Mar. 27, 2014, which are incorporated herein in their entireties by reference.

FIELD OF THE INVENTION

This invention relates to a photostable sunscreen composition for topical application.

BACKGROUND OF THE INVENTION

Ultraviolet (UV) light or radiation is classified as UVA, UVB and UVC depending upon the wavelength thereof, UVA being the longest of the three at 320-400 nm. UVA is further divided into two wavelength ranges, UVA I measuring 340-400 nm and UVA II measuring 320-340 nm. UVB wavelength ranges from 290 to 320 nm. Both the UVA and UVB radiations penetrate into the atmosphere and play an important role in causing health problems and conditions such as premature skin aging, eye damage (including cataracts) and skin cancers. Shorter rays of UVC in the wavelength range of 100 to 290 nm are mostly absorbed by the ozone layer and do not reach the earth. Harmful effects of UV-B radiation may be aggravated by UV-A radiation. In order to prevent and mitigate the harmful effects of exposure to UVA and UVB radiations, there are several sunscreen, cosmetic or dermatological formulations available for topical application to human skin or hair, which comprise one or more UV absorbers or UV filters.

UV filters used in the sunscreen preparations are mainly derivatives of 3-benzylidenecamphor, ethylhexyl salicylate, p-methoxy-cinnamic acid esters such as 2-ethylhexyl p-methoxycinnamate or octyl-methodycinnamate (2-ethylhexyl(2E)-3-(4-methoxyphenyl)pro-2-enoate) or dibenzoylmethane derivative such as 1-(4-methoxyphenyl)-3-(4-tert-butylphenyl)propane-1,3-dione or 4-(tert-butyl)-4'-methoxydibenzoyl methane (also called avobenzone, CAS No 70356-09-1). Some of the UV absorbing organic compounds employed in sunscreen compositions, avobenzone in particular, undergo rapid photo degradation on exposure to UV radiation and do not give effective protection from sun damage over a period of time. To overcome this problem, sunscreen preparations generally contain photostabilizers to enhance their photostability.

Deflandre et al teach stabilization of dibenzoylmethane derivative in a cosmetic composition comprising a cosmetically acceptable vehicle containing at least one fatty phase and alkyl β-β-diphenylacrylate or α-cyano-β-β-diphenylacrylate (U.S. Pat. No. 5,576,354). Raspanti et al teach photostable cosmetic compositions comprising combination of dibenzoylmethane derivative and benzopheride derivative (U.S. Pat. No. 5,776,439). Bonda et al describe a sunscreen composition comprising dibenzoylmethane derivative such as 4-(1,1-dimethylethyl)-4'-methoxydibenzoylmethane and a benzoate stabilizer for the dibenzoylmethane derivative (U.S. Pat. No. 5,788,954). Bonda et al also describes a sunscreen composition comprising dibenzoylmethane derivative stabilized with salicylate (U.S. Pat. No. 5,849,273).

Gonzenbach et al teach cosmetic compositions comprising at least one fatty phase, dibenzoymethane derivative and water soluble p-methoxycinnamate derivative stabilized with 3,3-diphenylacrylate derivative or benzylidene camphor derivative (U.S. Pat. No. 5,985,251). The term "water-soluble p-methoxycinnamate derivative" refers to compounds such as ammonium-, sodium-, potassium-p-methoxycinnamate, salts of primary, secondary or tertiary amines of p-methoxycinnamic acid like mono-, di- or tri-ethanol amine salts, aminomethyl-propanol salt, morpholine salt and the like. Preferred are mono-, di-, and triethanolamine salts. p-Methoxycinnamate derivative and 3,3-diphenylacrylate derivative are used as stabilizers for avobenzone.

Gonzenbach also teach photostable, cosmetic sunscreen composition comprising dibenzoylmethane derivative stabilized with α-cyano-β,β diphenylacrylate (U.S. Pat. No. 6,033,649). Cole et al teach sunscreen compositions comprising a dibenzoylmethane derivative stabilized with a combination of a benzophenone derivative and a diester or polyester of a naphthalene dicarboxylic acid (U.S. Pat. No. 6,444,195). Meyer et al describe sunscreen compositions containing avobenzone and zinc oxide stabilized with phenylbenzimidazole sulfonic acid (U.S. Pat. No. 7,244,416). Wagner et al teach a sunscreen composition comprising dibenzoylmethane derivative stabilized with merocyanine derivatives (U.S. Pat. No. 8,535,648).

Nambudiry et al teach a sunscreen composition suitable for topical application to human skin or hair to provide protection from excessive exposure to ultra-violet rays, which comprises an effective amount of a substituted 1,3-diketone which is 1,3-propanedione,1-(4-methoxy-5-benzofuranyl)-3-phenyl(pongamol) and physiologically acceptable vehicle for the substituted 1,3-diketone. The 1,3-diketone forms from 0.01 to 15% by weight of the composition. (U.S. Pat. No. 5,152,983).

In the above compositions, photostabilizers, wherever used, are all synthetic compounds which are generally considered to be unsafe for the users. Preparation of synthetic compounds generally gives rise to byproducts which create environmental hazards and problems. Octyl-methoxy cinnamate is oil soluble and water insoluble. Water-soluble p-methoxy cinnamate derivative and octyl-methoxy cinnamate are distinctly different compounds and are not chemical equivalents or substitutes for each other. Avobenzone is also oil soluble and water insoluble.

There is thus need for sunscreen compositions comprising and stabilized with natural photostabilizers, which are safe, environment friendly and cost effective.

DESCRIPTION OF INVENTION

To the best of our knowledge and information there are no known or reported sunscreen compositions for topical application comprising UV absorbers dibenzoylmethane derivative such as avobenzone(1-(4-methoxyphenyl)-3-(4-tert-butylphenyl)propane-1,3-dione), octyl-methoxycinnamate (2-ethylhexyl (2E)-3-(4-methoxyphenyl) prop-2-enoate) and 1-(4-methoxy-5-benzofuranyl)-3-phenyl 1,3 propanedione (pongamol) with or without additional UV absorbers consisting of methylene bis-benzotriazolyl tetramethylbutylphenol (Tinosorb M), ethyl hexyl triazone, octyl dimethyl PABA (para-aminobenzoic acid), TiO2 and ZnO. We have found out by extensive research and experimentation that photostable sunscreen composition for topical application comprising UV absorbers dibenzoylmethane derivative such as avobenzone, octyl-methoxycinnamate and pongamol with or without additional UV absorbers consisting of methylene bis-benzotriazolyl tetramethylbutylphenol (Tinosorb M), ethyl hexyl triazone, octyl dimethyl PABA (para-aminobenzoic acid), TiO2 and ZnO can be prepared by ingeniously and judiciously selecting the weight percentages of dibenzoylmethane derivative such as avobenzone, octyl-methoxycinnamate and pongamol and the weight percentage of additional UV filters consisting of methylene bis-benzotriazolyl tetramethylbutylphenol (Tinosorb M), ethyl hexyl triazone, octyl dimethyl PABA (para-aminobenzoic acid), TiO2 and ZnO, if any.

To the best of our knowledge and information, it is also not known or reported that pongamol is a photostabiliser and that it can stabilize sunscreen compositions for topical application comprising avobenzone and octyl-methoxy cinnamate with or without additional UV absorbers consisting of methylene bis-benzotriazolyl tetramethylbutylphenol (Tinosorb M), ethyl hexyl triazone, octyl dimethyl PABA (para-aminobenzoic acid), TiO2 and ZnO. We have also found out by extensive research and experimentation that using pongamol in judiciously and ingeniously selected weight percentages, sunscreen compositions comprising dibenzoylmethane derivative such as avobenzone and octyl-methoxycinnamate with or without additional UV filters consisting of methylene bis-benzotriazolyl tetramethylbutylphenol (Tinosorb M), ethyl hexyl triazone, octyl dimethyl PABA (para-aminobenzoic acid), TiO2 and ZnO, can be photostabilised by judiciously and ingeniously selecting the weight percentages of the avobenzone and octyl-methoxy cinnamate and additional UV absorbers, if any.

According to the invention there is provided a photostable sunscreen composition for topical application including dibenzoylmethane derivative and octyl-methoxy cinnamate and dermatologically acceptable excipients in combination with 1-(4-methoxy-5-benzofuranyl)-3-phenyl 1,3 propanedione (pongamol), wherein the dibenzoylmethane derivative is in 1 to 5% by weight of the composition, octyl-methoxycinnamate is in 1 to 10% by weight of the composition and dermatologically acceptable excipients are in 79 to 97% by weight of the composition and wherein the 1-(4-methoxy-5-benzofuranyl)-3-phenyl 1,3 propanedione (pongamol) is in 0.9 to 6% by weight of the composition and wherein the dermatologically active excipients contain 60-75% aqueous phase.

According to the invention there is also provided a photostable sunscreen composition for topical application including dibenzoylmethane derivative, octyl-methoxy cinnamate and methylene bis-benzotriazolyl tetramethylbutylphenol, ethyl hexyl triazone, octyl dimethyl PABA (para-aminobenzoic acid), TiO2 and ZnO and dermatologically acceptable excipients, in combination with 1-(4-methoxy-5-benzofuranyl)-3-phenyl 1,3 propanedione (pongamol), wherein the dibenzoylmethane derivative is in 1 to 5% by weight of the composition, octyl-methoxycinnamate is in 1 to 10% by weight of the composition and methylene bis-benzotriazolyl tetramethylbutylphenol, ethyl hexyl triazone, octyl dimethyl PABA (para-aminobenzoic acid), TiO2 and ZnO is in 14% by weight of the composition and dermatologically acceptable excipients are in 65 to 96% by weight of the composition and wherein the 1-(4-methoxy-5-benzofuranyl)-3-phenyl 1,3 propanedione (pongamol) is in 0.9 to 6% by weight of the composition and wherein the dermatologically active excipients contain 60-75% aqueous phase.

According to the invention there is also provided use of 1-(4-methoxy-5-benzofuranyl)-3-phenyl 1,3 propane dione (pongamol) to stabilize a sunscreen composition for topical application including dibenzoylmethane derivative and octyl-methoxy cinnamate and dermatologically acceptable excipients in combination with 1-(4-methoxy-5-benzofuranyl)-3-phenyl 1,3 propanedione (pongamol), wherein the dibenzoylmethane derivative is in 1 to 5% by weight of the composition, octyl-methoxycinnamate is in 1 to 10% by weight of the composition, and dermatologically acceptable excipients are in 79 to 97% by weight of the composition and wherein the 1-(4-methoxy-5-benzofuranyl)-3-phenyl 1,3 propanedione is in 0.9 to 6% by weight of the composition and wherein the dermatologically active excipients contain 60-75% aqueous phase.

According to the invention there is also provided use of 1-(4-methoxy-5-benzofuranyl)-3-phenyl 1,3 propane dione (pongamol) to stabilize a sunscreen composition for topical application including dibenzoylmethane derivative, octyl-methoxy cinnamate and methylene bis-benzotriazolyl tetramethylbutylphenol, ethyl hexyl triazone, octyl dimethyl PABA (para-aminobenzoic acid), TiO2 and ZnO and dermatologically acceptable excipients in combination with 1-(4-methoxy-5-benzofuranyl)-3-phenyl 1,3 propanedione (pongamol), wherein the diebenzoylmethane derivative is in 1 to 5% by weight of the composition, octyl-methoxycinnamate is in 1 to 10% by weight of the composition and methylene bis-benzotriazolyl tetramethylbutylphenol), ethyl hexyl triazone, octyl dimethyl PABA (para-aminobenzoic acid), TiO2 and ZnO is in 14% by weight of the composition and dermatologically acceptable excipients are in 65 to 96% be weight of the composition and wherein the 1-(4-methoxy-5-benzofuranyl)-3-phenyl 1,3 propanedione (pongamol) is in 0.9 to 6% by weight of the composition and wherein the dermatologically active excipients contain 60-75% aqueous phase.

Preferably, the 1-(4-methoxy-5-benzofuranyl)-3-phenyl 1,3 propanedione is used in 1 to 6% by weight of the composition. Preferably, the dibenzoylmethane derivative is in 1.5% to 5% by weight of the composition. Preferably, the dibenzoylmethane derivative is 1-(4-methoxyphenyl)-3-(4-tert-butyl phenyl propane-1,3-dione) or avobenzone and is of 90-100% purity. Preferably, the octyl-methoxycinnamate is in 8 to 10% by weight of the composition and is of 90-100% purity. Preferably, the 1-(4-methoxy-5-benzofuranyl)-3-phenyl 3 propanedione is of 90-98% purity. The sunscreen composition may be in any applicable form such as cream, lotion, gel, oil or spray.

Dermatologically acceptable excipients used in the sunscreen composition are those commonly used in sunscreen preparations. Dermatologically acceptable excipients include emollients such as coconut oil, palm kernel oil, silicone oil such as cyclomethicone or dimethicone, long chain fatty acids, fatty acid esters or waxes such as beeswax, candelilla, carnauba, polyethylene or paraffin; vitamins such as A, C, E, K or PP and derivatives or precursors thereof, alone or as mixtures thereof; antioxidants such as tocopheryl acetate or BHT (butylated hydroxytoluene); free-radical scavengers such as tocopheryl acetate or BHT (butylated hydroxytoluene); anti glycation agents such as carnosine green tea extract; calmatives such as C-β-D-xylopyranoside-2-bydroxypropane; NO-synthase inhibitors such as NG-monomethyl-L-arginine or methyl ester of NG-nitro-L-arginine; agents for stimulating the synthesis of dermal or epidermal macromolecules and/or for preventing their degradation such as globularia cordifolia extract; agents for stimulating fibroblast proliferation such as sophorolipid; agents for stimulating keratinocyte proliferation such as globularia cordifolia extract; muscle relaxants such as acetyl hexapeptide-3 or spilanthol.

Dermatologically acceptable excipients also include dermo-relaxing agents such as adenosine or manganese gluconate, keratolytic agents such as salicyclic acid; desquamating agents such as capryolyl salicyclic acid; moisturizers such as polyols such as glycerol, butylene glycol or propylene glycol; anti-inflammatory agents such as alpha bisabolol, *Portulaca oleraceae* extract; agents that act on the energy metabolism of cells such as euglena extract; insect repellents such as octyldodecyl neopentanoate; substance P or CGRP antagonists such as sendide or spantide II; anti-wrinkle agents such as argireline or knotgrass flavonoids; anti-ageing agents such as hyaluronic acid; astringent agents such as extract of gallnut or extract of centella; sebum-regulating agents and anti-seborrhoeic agents such as benzoyl peroxide or selenium disulphide; agents that protect formulation from microbials such as iodopropyl butylcarbamate.

The invention provides a photostable sunscreen composition for topical application comprising dibenzoylmethane derivative and octyl-methoxy cinnamate in combination with pongamol with or without additional UV filters consisting of methylene bis-benzotriazolyl tetramethylbutylphenol (Tinosorb M), ethyl hexyl triazone, octyl dimethyl PABA (para-aminobenzoic acid), TiO2 and ZnO in judiciously and ingeniously selected weight percentages and use of pongamol to photostabilize sunscreen composition for topical application comprising dibenzoylmethane derivative such as avobenzone and octyl-methoxycinnamate with or without additional UV filters consisting of methylene bis-benzotriazolyl tetramethylbutylphenol (Tinosorb M), ethyl hexyl triazone, octyl dimethyl PABA (para-aminobenzoic acid), TiO2 and ZnO in judiciously and ingeniously selected weight percentages.

Pongamol, a natural extract, is known to be safe in percentages up to 6%. Therefore, the sunscreen composition comprising pongamol in percentages up to 6% is safe for the users of the composition. Raw Material for the extract namely karanja seed oil is easily available. Extraction of pongamol is easy and convenient and cost effective and does not give rise to byproducts which are harmful to environment. Effective amount of pongamol required for stabilization of the UV absorbers is low. The invention is also thus efficient and cost effective.

Being also a sunscreen absorber, the sunscreen composition of the invention will have increased UV absorption efficiency and the increased UV absorption efficiency of the composition will be maintained for a longer duration because of the photostability of the composition imparted by the pongamol.

Because the sunscreen composition of the invention comprises 60-75% aqueous phase, it has excellent moisturing effect which is highly desirable. In spite of the high aqueous phase, it has been possible according to the invention to obtain photostable sunscreen composition with water insoluble octyl-methoxy cinnamate and avobenzone thereby clearly establishing the synergy of the sunscreen composition.

The following experimental examples are illustrative of the invention but not limitative of the scope thereof:

EXAMPLE 1A

Comparative spectrophotometric studies of sunscreen compositions with and without pongamol were carried out to determine their physical and chemical stability to UV light according to the test procedures described in the literature ["A statistical application allowing comparison between the spectrums of two or several products to evaluate if they are statistically equivalent", D. Lutz and S. Miksa. In vitro comparison—A new accessible and reliable statistical method to compare the global UV protection properties of cosmetics. H&PCToday and Monographic supplement SUN CARE—Vol 8 (4) July/August 2013, P23-27 by Helio Screen.]. The sunscreen compositions used in the studies were those in the following Table IA:

TABLE IA

| Constituents (INCI Names) | Sunscreen composition 1 | Sunscreen composition 2 | Sunscreen composition 3 | Sunscreen composition 4 | Sunscreen composition 5 | Sunscreen composition 6 |
| --- | --- | --- | --- | --- | --- | --- |
| Octylmethoxy Cinnamate (98% purity) % | 8.00 | 8.00 | 8.00 | 8.00 | 8.00 | 8.00 |
| Avobenzone (98% purity) % | 3.00 | 3.00 | 3.00 | 3.00 | 3.00 | 3.00 |
| Pongamol (98% purity) % | 0.00 | 0.20 | 0.50 | 1.00 | 3.00 | 6.00 |
| Hydrogenated Polydecene % | 6.50 | 6.50 | 6.50 | 6.50 | 6.50 | 6.50 |
| Dimethicone% | 3.50 | 3.50 | 3.50 | 3.50 | 3.50 | 3.50 |
| Propylene Glycol % | 1.50 | 1.50 | 1.50 | 1.50 | 1.50 | 1.50 |
| Isopropyl Myristate % | 1.50 | 1.50 | 1.50 | 1.50 | 1.50 | 1.50 |
| Emulsifying Wax NF % | 1.50 | 1.50 | 1.50 | 1.50 | 1.50 | 1.50 |
| Glyceryl Stearate and PEG (polyethylene glycol)-100 Stearate % | 1.50 | 1.50 | 1.50 | 1.50 | 1.50 | 1.50 |
| Cetyl Alcohol % | 1.50 | 1.50 | 1.50 | 1.50 | 1.50 | 1.50 |
| Triethanolamine % | 1.50 | 1.50 | 1.50 | 1.50 | 1.50 | 1.50 |
| Stearic Acid % | 1.50 | 1.50 | 1.50 | 1.50 | 1.50 | 1.50 |
| Phenoxyethanol % | 0.65 | 0.65 | 0.65 | 0.65 | 0.65 | 0.65 |
| Fragrance % | 0.30 | 0.30 | 0.30 | 0.30 | 0.30 | 0.30 |
| Vitis Vinifera (Grapeseed) Oil % | 0.30 | 0.30 | 0.30 | 0.30 | 0.30 | 0.30 |
| Citrullus Lanatus (Watermelon) Fruit Extract and Citrullene % | 0.30 | 0.30 | 0.30 | 0.30 | 0.30 | 0.30 |
| Carbomer % | 0.30 | 0.30 | 0.30 | 0.30 | 0.30 | 0.30 |
| Butylated Hydroxytoluene | 0.75 | 0.75 | 0.75 | 0.75 | 0.75 | 0.75 |
| Glutathione % | 0.075 | 0.075 | 0.075 | 0.075 | 0.075 | 0.075 |
| Alpha Arbutin % | 0.075 | 0.075 | 0.075 | 0.075 | 0.075 | 0.075 |
| Water % | Qs | Qs | Qs | Qs | Qs | Qs |

Emulsifying wax NF is a blend of cetearyl alcohol and polysorbate 60 marketed by Lotion crafter.

Fragrance—blend of Romance For Women C-3722/2, Sampaguita 040161 and Forever Romance E31033 of Eurochemicals Inc.

The sunscreen compositions were exposed to UV, 4.8 (Minimal Erythemal Dose) which is equivalent to 72 min exposure to the zenith sun with erythemal power of 4 MED/h. After normalization of the evolution of the level of sun protection of the sunscreen compositions while being UV exposed, root mean square error (RMSE) values of the sunscreen compositions were calculated and were as given in the following Table IIA:

TABLE IIA

| | Sunscreen cream | | | | | |
|---|---|---|---|---|---|---|
| | Sunscreen composition 1 without pongamol | Sunscreen composition 2 with pongamol at 0.2% | Sunscreen composition 3 with pongamol at 0.5% | Sunscreen composition 4 with pongamol at 1.0% | Sunscreen composition 5 with pongamol at 3.0% | Sunscreen composition 6 with pongamol at 6.0% |
| Tolerance threshold of RMSE | 5% | 5% | 5% | 5% | 5% | 5% |
| RMSE percent calculated | 18% | 17% | 13% | 7% | 5% | 2% |

The calculated RMSE percent values in Table IIA show that pongamol in concentrations of 3 and 6% by weight are very effective in stabilizing the sunscreen compositions 5 and 6 comprising 3% by weight of avobenzone and 8% by weight of octylmethoxycinnamate, respectively and that the sunscreen composition 1 without pongamol are not photostable. Whereas the calculated RMSE percent values in Table 1 of Example 2 of the provisional specification show that pongamol in about 0.9% by weight onwards very effectively stabilizes sunscreen compositions comprising 1.5% by weight avobenzone and 8% by weight octyl methoxy cinnamate. The study results show that the percentage of pongamol for stabilization of the sunscreen composition increases with the percentage increase of avobenzone thereby clearly establishing the synergy of stabilization of the sunscreen composition with pongamol.

EXAMPLE 2A

Comparative spectrophotometric studies were conducted on commercially available sunscreen compositions consisting of avobenzone (1.5% by wt, 98% purity) and octyl-methoxycinnamate (8% by wt, 98% purity) and dermatologically acceptable excipients (Laboratoire Onyligne, France Helioscreen reference 21ONY01-1013R&D3849) without pongamol and with different concentrations of pongamol of 98% purity according to the test procedure described in Example 1A. The results were as given in the Table IIIA below:

TABLE IIIA

| | Sunscreen composition without pongamol | Sunscreen composition with pongamol at 0.2% | Sunscreen composition with pongamol at 0.5% | Sunscreen composition with pongamol at 1.0% | Sunscreen composition with pongamol at 3.0% | Sunscreen composition with pongamol at 6.0% |
|---|---|---|---|---|---|---|
| Tolerance threshold of RMSE | 5% | 5% | 5% | 5% | 5% | 5% |
| RMSE percent calculated | 28.7% | 26% | 13% | 3% | 3% | 3% |

The calculated RMSE percent values as obtained in the Table IIIA are in agreement with those in Table 1 of Example 2 of the provisional specification and clearly show that pongamol in concentrations of about 0.9% by weight is very effective in stabilizing the sunscreen creams comprising 1.5% by weight avobenzone and 8% by weight octyl-methoxy cinnamate and that the cream composition without pongamol is not photostable. The study results also establish the weight relationship between pongamol and avobenzone in stabilizing the sunscreen compositions with different weight percentages of pongamol as found in Example 1A.

EXAMPLE 3A

Comparative spectrophotometric studies were conducted on commercially available sunscreen composition consisting of 3% by wt avobenzone of 98% purity, 8% by wt octyl-methoxycinnamate of 98% purity, 14% by wt of other UV filters consisting of methylene bis-benzotriazolyl tetramethylbutylphenol (Tinosorb M), ethyl hexyl triazone, cctyl dimethyl PABA (para-aminobenzoate), TiO$_2$ and ZnO and dermatologically acceptable excipients [Laboratoire Onyligne, France, Creme Solaire SPF50 (Helioscreen reference 18ONY03-1010He123a2261)] with and without pongamol (1% by wt and 98% purity) and the results were as shown in the following Table IVA:

TABLE IVA

| | Sunscreen composition without pongamol | Sunscreen composition with pongamol |
|---|---|---|
| Tolerance threshold of RMSE | 5% | 5% |
| RMSE percent calculated | 8.7% | 4.63% |

The calculated RMSE percent values in Table IVA are in agreement with those in the Table 2 of Example 3 of the provisional specification and clearly show that pongamol in concentrations of about 0.9% by weight is very effective in stabilizing the sunscreen composition comprising 3% by weight avobenzone, 8% by weight octylmethoxycinnamate and 14% by weight of the other UV filters and that the sunscreen composition without pongamol is not photostable. The study results also show that when the sunscreen composition comprises the other UV filters, the percentage of pongamol for effective stabilization of the sunscreen composition can be low of the order of about 1% even if the avobenzone percentage is 3%. The study results also clearly establish the synergy of stabilization of the sunscreen composition comprising the various UV filters with pongamol.

The invention claimed is:

1. A photostable sunscreen composition for topical application comprising:
   dibenzoylmethane derivative;
   octylmethoxy cinnamate; and
   dermatologically acceptable excipients;
   in combination with:
   1-(4-methoxy-5-benzofuranyl)-3-phenyl 1,3 propanedione (pongamol),
   wherein:
   the dibenzoylmethane derivative is 1 to 5% by weight of the composition
   the octylmethoxy cinnamate is 7 to 10% by weight of the composition;
   the dermatologically acceptable excipients are 79 to 97% by weight of the composition and contain 60-75% aqueous phase comprising:
   6.50% by weight hydrogenated polydecene;
   3.50% by weight dimethicone;
   1.50% by weight propylene glycol;
   1.50% by weight isopropyl myristate;
   1.50% by weight emulsifying wax NF (blend of cetearyl alcohol and polysorbate 6.0);
   1.50% by weight glyceryl stearate and PEG (polyethylene glycol)-100 stearate;
   1.50% by weight cetyl alcohol;
   1.50% by weight triethanolamine;
   1.50% by weight stearic acid;
   0.65% by weight phenoxyethanol;
   0.30% by weight fragrance;
   0.30% by weight *vitis vinifera* (grapeseed) oil;
   0.30% by weight *citrullus lanatus* (watermelon) fruit extract and citrullene;
   0.30% by weight carbomer;
   0.75% by weight butylated hydroxytoluene;
   0.075% by weight glutathione;
   0.075% by weight alpha arbutin and
   balance % water; and
   wherein the composition is stabilized with the 1-(4-methoxy-5-benzofuranyl)-3-phenyl 1,3 propanedione (pongamol) having 90-98% purity in 0.9 to 6% by weight of the composition.

2. A photostable sunscreen composition for topical application, comprising:
   dibenzoylmethane derivative;
   octylmethoxy cinnamate;
   methylene bis-benzotriazolyl tetramethylbutylphenol, ethyl hexyl triazone, octyl dimethyl PABA (para-aminobenzoic acid), TiO2 and ZnO; and
   dermatologically acceptable excipients;
   in combination with:
   1-(4-methoxy-5-benzofuranyl)-3-phenyl 1,3propanedione (pongamol),
   wherein:
   the dibenzoylmethane derivative is 1 to 5% by weight of the composition;
   the octylmethoxy cinnamate is 7 to 10% by weight of the composition;
   the methylene bis-benzotriazolyl tetramethylbutylphenol, ethyl hexyl triazone, octyl dimethyl PABA (para-aminobenzoic acid), TiO$_2$ and ZnO are in 14% by weight of the composition;
   the dermatologically acceptable excipients are 65 to 96% by weight of the composition and-contain 60-75% aqueous phase comprising:
   6.50% by weight hydrogenated polydecene;
   3.50% by weight dimethicone;
   1.50% by weight propylene glycol;
   1.50% by weight isopropyl myristate;
   1.50% by weight emulsifying wax NF (blend of cetearyl alcohol and polysorbate 6.0);
   1.50% by weight glyceryl stearate and PEG (polyethylene glycol)-100 stearate;
   1.50% by weight cetyl alcohol;
   1.50% by weight triethanolamine;
   1.50% by weight stearic acid;
   0.65% by weight phenoxyethanol;
   0.30% by weight fragrance;
   0.30% by weight *vitis vinifera* (grapeseed) oil;
   0.30% by weight *citrullus lanatus* (watermelon) fruit extract and citrullene;
   0.30% by weight carbomer;
   0.75% by weight butylated hydroxytoluene;
   0.075% by weight glutathione;
   0.075% by weight alpha arbutin and
   balance % water; and
   wherein the composition is stabilized with the 1-(4-methoxy-5-benzofuranyl)-3-phenyl 1,3 propanedione (pongamol) having 90-98% purity in 0.9 to 6% by weight of the composition.

3. The sunscreen composition as claimed in claim 1, wherein the 1-(4-methoxy-5-benzofuranyl)-3-phenyl 1,3 propanedione is 1 to 6% by weight of the composition.

4. The sunscreen composition as claimed in claim 1, wherein the dibenzoylmethane derivative is 1.5% to 5% by weight of the composition.

5. The sunscreen composition as claimed in claim 1, wherein the dibenzoylmethane derivative is 1-(4-methoxyphenyl)-3-(4-tert-butylphenyl) propane-1,3-dione and is of 90-100% purity.

6. The sunscreen composition as claimed in claim 1, wherein the octylmethoxy cinnamate is of 90-100% purity.

7. The sunscreen composition as claimed in claim 1, being a cream, lotion, gel, oil or spray.

8. A photostable sunscreen composition for topical application, comprising:
   dibenzoylmethane derivative;
   octylmethoxycinnimate; and
   dermatologically acceptable excipients;
   in combination with:
   1-(4-methoxy-5-benzofuranyl)-3-phenyl 1,3-propanedione (pongamol);
   wherein:
   the octylmethoxy cinnamate is 8.00% by weight of the composition and is 98% purity, the dibenzoylmethane derivative is 1-(4-methoxyphenyl)-3-(4-tert-butylphenyl) propane-1,3-dione in 3.00% by weight of the composition and is 98% purity;
   the dermatologically acceptable excipients are 79 to 97% by weight of the composition containing 60-75% aqueous base and comprise:
   6.50% by weight hydrogenated polydecene;
   3.50% by weight dimethicone;
   1.50% by weight propylene glycol;
   1.50% by weight isopropyl myristate;
   1.50% by weight emulsifying wax NF (blend of cetearyl alcohol and polysorbate 6.0),
   1.50% by weight glyceryl stearate and PEG (polyethylene glycol)-100 stearate;

1.50% by weight cetyl alcohol;
1.50% by weight triethanolamine;
1.50% by weight stearic acid;
0.65% by weight phenoxyethanol;
0.30% by weight fragrance;
0.30& by weight *vitis vinifera* (grapeseed) oil;
0.30% by weight *citrullus lanatus* (watermelon) fruit extract and citrullene;
0.30% by weight carbomer;
0.75% by weight butylated hydroxytoluene;
0.075% by weight glutathione;
0.075% by weight alpha arbutin; and
balance % water; and
the 1-(4-methoxy-5-benzofuranyl)-3-phenyl 1,3 propane-dione is 3.00% by weight of the composition and is of 98% purity.

9. A photostable sunscreen composition for topical application, comprising:
dibenzoylmethane derivative;
octylmethoxycinnimate; and
dermatologically acceptable excipients;
in combination with:
1-(4-methoxy-5-benzofuranyl)-3-phenyl 1,3-propane-dione (pongamol);
wherein:
the octylmethoxy cinnamate is in 8.00% by weight of the composition and is of 98% purity,
the dibenzoyl methane derivative is 1-(4-methoxyphenyl)-3-(4-tert-butylphenyl) propane-1,3-dione in 3.00% by weight of the composition and is of 98% purity;
the dermatologically acceptable excipients are 79 to 97% by weight of the composition containing 60-75% aqueous base and comprise:
6.50% by weight hydrogenated polydecene;
3.50% by weight dimethicone;
1.50% by weight propylene glycol;
1.50% by weight isopropyl myristate;
1.50% by weight emulsifying wax NF (blend of cet-earyl alcohol and polysorbate 6.0);
1.50% by weight glyceryl stearate and PEG (polyethylene glycol)-100 stearate;
1.50% by weight cetyl alcohol;
1.50% by weight triethanolamine;
1.50% by weight stearic acid;
0.65% by weight phenoxyethanol;
0.30% by weight fragrance;
0.30% by weight *vitis vinifera* (grapeseed) oil;
0.30% by weight *citrullus lanatus* (watermelon) fruit extract and citrullene;
0.30% by weight carbomer;
0.75% by weight butylated hydroxytoluene;
0.075% by weight glutathione;
0.075% by weight alpha arbutin; and
balance % water; and
the 1-(4-methoxy-5-benzofuranyl)-3-phenyl 1,3propane-dione is in 6.00% by weight of the composition and is of 98% purity.

10. The sunscreen composition as claimed in claim 1, comprising:
8% by weight octylmethoxy cinnamate of 90-100% purity;
1.5% by weight of 1-(4-methoxyphenyl)-3-(4-tert-butylphenyl) propane-1,3-dione (avobenzone) of 90-100% purity;
80 to 90% by weight of dermatologically acceptable excipients; and
1% by weight of 1-(4-methoxy-5-benzofuranyl)-3-phenyl 1,3 propanedione (pongamol) of 90-98% purity.

11. The sunscreen composition as claimed in claim 1, comprising:
8% by weight octylmethoxy cinnamate of 90-100% purity;
1.5% by weight of 1-(4-methoxyphenyl)-3-(4-tert-butylphenyl) propane-1,3-dione (avobenzone) of 90-100% purity;
87 to 88% by weight of dermatologically acceptable excipients; and
3% by weight of 1-(4-methoxy-5-benzofuranyl)-3-phenyl 1,3 propanedione (pongamol) of 90-98% purity.

12. The sunscreen composition as claimed in claim 1, comprising:
8% by weight octylmethoxy cinnamate of 90-100% purity;
1.5% by weight of 1-(4-methoxyphenyl)-3-(4-tert-butylphenyl) propane-1,3-dione (avobenzone) of 90-100% purity;
84 to 85% by weight of dermatologically acceptable excipients; and
6% by weight of 1-(4-methoxy-5-benzofuranyl)-3-phenyl 1,3 propanedione (pongamol) of 90-98% purity.

13. The sunscreen composition as claimed in claim 2, wherein the 1-(4-methoxy-5-benzofuranyl)-3-phenyl 1,3 propanedione is 1 to 6% by weight of the composition.

14. The sunscreen composition as claimed in claim 2, wherein the dibenzoylmethane derivative is 1.5% to 5% by weight of the composition.

15. The sunscreen composition as claimed in claim 2, wherein the dibenzoylmethane derivative is in 1-(4-methoxyphenyl)-3-(4-tert-butylphenyl) propane-1,3-dione (avobenzone) and is of 90-100% purity.

16. The sunscreen composition as claimed in claim 2, wherein the octylmethoxy cinnamate is 7 to 10% of the composition and is of 90-100% purity.

17. The sunscreen composition as claimed in claim 2, being a cream, lotion, gel, oil or spray.

* * * * *